United States Patent
Havel et al.

(10) Patent No.: US 7,200,434 B2
(45) Date of Patent: Apr. 3, 2007

(54) CONTROL OF ARBITRARY WAVEFORMS FOR CONSTANT DELIVERED ENERGY

(75) Inventors: William J. Havel, Maple Grove, MN (US); Paul J. Degroot, Brooklyn Park, MN (US); Thomas W. Sinner, New Brighton, MN (US); Kevin Kuehn, Shoreview, MN (US); Gary Kemmetmueller, Rogers, MN (US); Warren W. Wold, Edina, MN (US)

(73) Assignee: Medtronic, Inc., Minneapolis, MN (US)

(*) Notice: Subject to any disclaimer, the term of this patent is extended or adjusted under 35 U.S.C. 154(b) by 69 days.

(21) Appl. No.: 11/089,798

(22) Filed: Mar. 25, 2005

(65) Prior Publication Data

US 2005/0228453 A1   Oct. 13, 2005

(51) Int. Cl.
*A61N 1/39* (2006.01)
(52) U.S. Cl. .................. 607/8; 607/5; 607/6; 607/7; 607/62
(58) Field of Classification Search .............. 607/5–8, 607/62–64
See application file for complete search history.

(56) References Cited

U.S. PATENT DOCUMENTS 5,201,865 A * 4/1993 Kuehn ..................... 607/8
5,999,582 A * 12/1999 Rice ..................... 375/377
6,208,898 B1 * 3/2001 Gliner et al. .................. 607/8
6,241,751 B1 * 6/2001 Morgan et al. ................ 607/8
6,546,287 B1 * 4/2003 Havel et al. ................. 607/7
6,647,290 B2 * 11/2003 Wuthrich .................... 607/5

OTHER PUBLICATIONS

Huang et al. "Defibrillation Waveforms". Nonpharmacological Therapy of Arrhythmias. 1998. pp. 367-383.*

* cited by examiner

*Primary Examiner*—Robert Pezzuto
*Assistant Examiner*—Yun Haeng Lee
(74) *Attorney, Agent, or Firm*—Paul H. McDowell; Girma Wolde-Michael

(57) ABSTRACT

The present invention outlines structures and methods for delivering a controllable amount of energy to a patient by automatically compensating for the load impedance detected by an implantable-cardioverter defibrillator (ICD). The invention employs high speed, switching power converter technology for the efficient generation of high energy, arbitrary waveforms. Unlike a linear amplifier, switching power converters deliver high-energy waveforms with an efficiency that is independent of the size and amplitude of the desired waveform. An ICD that uses a switching power converter to deliver the desired energy to the patient stores the energy to be delivered in a storage capacitor. The converter then transforms this energy into an arbitrarily shaped output voltage-controlled or current-controlled waveform by switching the storage capacitor in and out of the output circuit at a high rate of speed. Preferably, the waveform comprises a ramp-type waveform.

17 Claims, 10 Drawing Sheets

| Example 1 (Single Toroid, Magnetics Core Selector Chart Method L = 14 μH) | Example 2 (Single Toroid, L = 14 μH) | Example 3 (2 stacked toroids, L = 14 μH) |
|---|---|---|
| Ll²=12 from selector chart choose 58350-A2<br>58350-A2 perm. 125μ $A_L$=105 L=5.88 cm | 58043-A2 perm. 14μ $A_L$=7 l=2.38 cm | 58273-A2 perm. 14μ $A_L$=12 L=1.363 |
| N=1000*(0.014/105)^0.5=11.5 | N=1000*(0.014/7)^0.5=44.7 | N=1000*(0.014//2*12)^0.5=24 |
| H=(0.4*PI*11.5*40)/5.88=99 (design manual table: ~33% perm. at Ip<br>So Inductance falls to 0.33*14μH=4.6 μH at 40 Amps | H=(0.4*PI*44.7*40)/2.38=944 (design manual table: ~71% perm. at Ip<br>So Inductance falls to 0.71*14μH=9.9 μH at 40 Amps | H=(0.4*PI*24*30)/1.363=884 (design manual table: ~72% perm. at Ip<br>So Inductance falls to 0.72*14μH=10.0 μH at 40 Amps |
| Volume = 5.2 cc (diameter=24.6 mm, length = 10.9 mm) | Volume = 0.59 cc (diameter=11.2 mm, length = 5.96 mm) | Volume = 0.53 cc (diameter=7.6 mm, length = 11.7 mm) | a. Magnetics, Inc. Is a proprietary firm with which Medtronic worked to build and test representative models of the inductor cores cited in these examples.

FIG. 8

CONTROL OF ARBITRARY WAVEFORMS FOR CONSTANT DELIVERED ENERGY

CROSS REFERENCE TO RELATED APPLICATION

The present patent disclosure claims the benefit of a prior provisional U.S. patent application entitled, "Control of Arbitrary Waveforms for Constant Delivered Energy," filed on 3 Dec. 2001 as application Ser. No. 60/337,135 and the contents of which are hereby incorporated herein.

FIELD OF THE INVENTION

The present invention relates generally to cardiac stimulators.

Specifically, this invention relates to the generation of defibrillation waveforms for delivery to the heart to break ventricular fibrillation and restore a normal cardiac rhythm. More specifically, the present invention presents an apparatus and method of delivering a controllable amount of energy by automatically compensating for the load impedance sensed by the implantable defibrillator.

BACKGROUND OF THE INVENTION

Prior art ICD circuitry delivers energy to the patient by discharging a charged capacitor into electrodes that are in direct contact with the patient's heart. In those ICDs, total energy is limited by controlling the amount of stored energy on the capacitor, which, in turn, limits the charge voltage. Typically, the shock is truncated when voltage on the capacitor decays to a known value. The resulting waveform exhibits an exponential decay with a constant tilt. The tilt is the percentage by which the waveform voltage decays from start to end. Accordingly, patients with larger load impedances will receive longer shocks because it will take a longer time for the waveform voltage to decay.

Waveforms used in implantable defibrillators to defibrillate a patient have been, for the most part, truncated exponential waveforms. Truncated exponential waveforms are generated by charging the capacitor(s) and discharging it through the total impedance, which includes the impedance of the patient and the leads used to deliver the waveform. Truncation has been used clinically because of the concern that the long, low tail end of a non-truncated exponential waveform might re-induce fibrillation.

In spite of its limitations, manufacturers of implantable cardioverter-defibrillators (ICDs) continue to use truncated exponential waveforms for clinical settings. Moreover, ICD manufacturers have long produced ICDs with programmable shock strengths. The strength of the shock required to defibrillate, is controlled by the time constant (TC) and tilt (T) of the truncated exponential waveform. TC is defined as the time required for the shock voltage to decrease to a preset percentage of its starting value and T is the percentage of leading edge voltage remaining at the trailing edge of the waveform. Altering the duration of the waveform while maintaining the same TC will change T. Altering TC while holding waveform duration constant will change T. T can additionally be changed by modifying both TC and waveform duration.

Monophasic truncated exponential waveforms were generally used until biphasic truncated exponential waveforms were introduced. Biphasic waveforms are created by a switch in the capacitance that reverses the polarities delivered to the electrodes during delivery of the shock pulse.

Some biphasic waveforms are thought to have lower defibrillation thresholds (DTs), compared to monophasic waveforms. This is particularly true when the first phase of the biphasic waveform delivers more energy than the second phase.

In addition to the types of waveform used, the determination of which electrode functions as the anode in the right ventricle appears to lower the DT when a monophasic waveform is used. Such a determination of the electrode polarity, however, appears to have little influence when biphasic waveforms are used. Clinicians, however, generally err on the side of caution and program the right ventricular electrode as the anode when using a biphasic waveform.

A published study by Huang et al., "Defibrillation Waveforms" in *Nonpharmacological Therapy of Arrhythmias for the 21$^{st}$ Century: The State of the Art*, Futura, 1998 concludes: "Thus, the (truncated exponential) biphasic waveform appears to be more efficacious for defibrillation than the (truncated exponential) monophasic waveform for internal as well as external defibrillation and for ventricular as well as atrial defibrillation." This same study, in its opening paragraph, states: "Schuder, et al (in *Circ Res*, 1966, 19: 689–694) have shown that for external defibrillation in the dog, a waveform consisting of an ascending ramp has a much higher success rate for defibrillation than a descending ramp waveform of the same strength." Despite this fact, there has been little research and/or implementation of the ascending ramp. This may be because waveforms similar to the descending ramp are much easier to generate, the descending ramp type of waveform is used clinically even though it is much less efficient for defibrillation.

In U.S. Pat. No. 5,725,560, Brink describes a method of delivering arbitrary waveforms with a computer-controlled system. The basic energy converter topology disclosed is a buck, or step-down, type of power converter with a pulse width modulation control scheme. This type of power converter is a common topology used in the field of energy conversion. The circuitry developed in the '560 patent is implemented as a full bridge (H-bridge) dc-dc converter that enables biphasic waveforms. The system monitors the voltage and current delivered to the patient and uses these parameters as a control feedback.

Weiss, in U.S. Pat. No. 5,184,616, teaches an arbitrary waveform circuit for use in ICDs. As in the '560 patent, a switching power converter is used with a full bridge (H-bridge) implementation. The '616 patent has a control scheme with a predetermined pulse width or duty cycle for each switching cycle during delivery of the waveform. In some cases, an impedance measurement is required to determine the proper timing. This impedance measurement uses a constant current source by applying current to the patient and then computing measured applied voltage over applied current. A feedback element receives signal information from the output of the filter circuit. Based on this input, the circuit assumes that the output to the patient is monitored so that the microprocessor can make adjustments to the shock control, charge control, and dump control lines.

Imran, in U.S. Pat. No. 4,768,512, describes a method of delivering a truncated exponential waveform that is "chopped" or comprised of a train of high frequency, exponentially decaying pulses delivered from a storage capacitor. In this patent, when a feedback signal on the patient load drops below a reference voltage, the output voltage is disabled, resulting in a waveform truncation.

Brewer, et al. have been granted a number of patents relating to the control and delivery of various defibrillation waveforms. For example, in U.S. Pat. No. 5,908,442, Brewer et al. discloses a method of delivering biphasic truncated damped sine wave shocks. Two discharge circuits that operate in succession allow delivery of biphasic wave shocks. The truncation time of the shock is determined using the Blair equivalent circuit model of defibrillation together with knowledge of distributed impedances of the chest wall, thorax, lung, and heart. This method requires that the total patient impedance be known before shock delivery.

Brewer et al., in U.S. Pat. No. 5,991,658, describes a method of continuously determining the tilt of a truncated exponential waveform based on repeated discrete measurements of the impedance or resistance of the patient. When the storage capacitors decay to the point where an optimal tilt based on defibrillation efficacy models, equals the computed tilt the waveform is then truncated.

Further, Brewer et al. in U.S. Pat. No. 5,978,706 teaches a method of continuously determining the truncation point of a damped sinusoidal waveform, similar to that described in the '442 patent, but applied to the delivery of a sinusoidal waveform. The '706 patent discloses a method of truncation that requires measurement of the patient's resistance. Specifically, a pre-calculated design rule to determine truncation time based on patient impedance that is continuously measured and discretely updated during delivery of the waveform is implemented. This method relies on a measurement of impedance prior to shock delivery, rather than a real-time impedance measurement during shock delivery.

Lerman, in U.S. Pat. Nos. 4,574,810, 4,771,781, and 5,088,489 discloses a method of delivering sinusoidal current to transthoracic defibrillation paddles/electrodes and then measuring the resultant voltage across the electrodes. This voltage is then used to determine the patient's transthoracic resistance. The resistance value is then used to scale a subsequent shock by scaling the voltage to which the capacitor is charged prior to shock delivery. The method is equivalent to a current-based process, because the peak current of the waveform becomes the controlling parameter.

Charbonnier, et al, in U.S. Pat. No. 4,328,808, proposes a method of computing transthoracic resistance given a predetermined stored energy and, by measurement of peak output current, to perform computations during delivery of a damped sine waveform. These data are used to determine delivered energy and to trigger an audible alarm if the resistance falls outside a preset boundary. In U.S. Pat No. 5,111,813, Charbonneier et al. specify an "impedance normalized delivered energy" in lieu of current.

Gliner et al., in U.S. Pat. Nos. 5,593,427, 5,601,612, 5,607,454, 5,620,470, 5,735,879, 5,749,904, 5,749,905, 5,776,166, 5,803,927, 5,836,978, 6,047,212, disclose a method for delivering a truncated exponential waveform to a patient. As the pulse is delivered, the voltage remaining on the storage capacitor is monitored. Under certain circumstances, the waveform or its first phase is truncated when the voltage decays to a certain value. However, if too little or too much time passes, the waveform may be truncated early or late.

Lopin and Avati, in U.S. Pat. Nos. 5,733,310, 5,769,872, 5,797,968, 5,800,462, 5,800,463, 5,904,706, 6,096,063, describe a method of measuring patient resistance by using a "sensing pulse" applied immediately before defibrillator discharge. This pulse is applied as a voltage and the resulting current is then measured and used to compute resistance.

In U.S. Pat. No. 5,201,865, Kuehn discloses a method of measuring lead impedance by measuring the time it takes a capacitor to discharge through a precision resistor and then comparing this time to the time required to discharge the same capacitor through the patient load.

In U.S. Pat. Nos. 5,549,643 and 5,645,573, Kroll and Smith describe a method of timing the duration of a capacitor-discharge truncated exponential waveform defibrillation shock by first waiting for the capacitor voltage to decay by a certain percent. Then it extends the waveform by a fixed duration beyond this percentage.

In a Ph.D. thesis, entitled "A Controlled-Power Arbitrary Waveform Method of Defibrillation" (March 2000, Purdue University), Havel presents a method for instantaneously controlling output power to the load without measuring output current or load resistance. This method uses a pulse width modulator control scheme that uses the voltage on the storage capacitor as a feedback parameter. Thus, output power is controlled by actively calculating the rate of decay of the energy storage capacitor.

In U.S. Pat. Nos., 5,481,238, issued to Carsten, et al., U.S. Pat. No. 5,629,842, issued to Johnson, et al., and U.S. Pat. No. 5,165,162 issued to Charles, there are descriptions of how compound inductors may be assembled in buck and boost regulators. For example, a toroidal inductor member formed from a plurality of turns of wire is described in the '842 patent, including an inductor with a segmented toroidal core with a winding wound thereon in the '162 patent.

Typically, ICDs have the capability of providing a variety of defibrillation waveforms. In the main, these waveforms have either been monophasic or biphasic waveforms applied as truncated exponential waveform pulses. Clinically, however, there is a need for an apparatus and method that would take account of changes in patient resistance. A patient's impedance changes due to any of a wide variety of causes, the defibrillation waveform pulse may provide far less energy than what the physician has programmed. Thus, there is a need for new methods to provide a consistent amount of energy in the presence of varying impedances, as is disclosed in the present invention.

SUMMARY OF THE INVENTION

The present invention outlines a structure method for delivering a controllable amount of energy to a patient by automatically compensating for the load impedance detected by the ICD.

The advent of high speed, switching power converters has made possible the generation of high energy, arbitrary waveforms at high efficiencies. Unlike a linear amplifier, switching power converters can deliver a high-energy waveform with an efficiency that is independent of the size and amplitude of the desired waveform. A linear amplifier must be supplied with a higher voltage than desired for the output. The ICD circuit must then drop this voltage to the required energy through a lossy element to achieve the desired output voltage or current. An ICD that uses a switching power converter to deliver the desired energy to the patient stores the energy to be delivered in a capacitor. The converter then transforms this energy into an arbitrarily shaped output voltage or current waveform by switching the storage capacitor in and out of the output circuit at a high rate of speed.

A practical system using the present invention will experience some energy loss in the conversion process. This loss can be compensated for via the ability to optimally control the duration and shape of the output waveform. Several waveforms, including an ascending waveform have been shown, both theoretically and clinically, to defibrillate with less delivered energy than the traditional capacitor discharged, truncated exponential waveform. Theoretical constructs and clinical evidence demonstrate that most waveforms defibrillate more effectively at a specific duration.

The instantaneous power requirements of a defibrillation shock are in the order of 3 kW for an ICD. This level of power is too high to be instantaneously drawn from a battery. Thus, even with a switching power converter, an ICD with arbitrary waveform capability would need to pre-store the shock energy in another circuit element, such as a capacitor. Although switching power converters have the capability of boosting or reducing output voltage or current with respect to input, there is a practical constraint. The total energy going out of the converter plus the efficiency losses must equal the energy going into the system. The energy within the pre-storage capacitor thus constrains the waveform-delivered energy. Therefore, to prevent waveforms from being distorted as energy on this capacitor is completely consumed, a method of controlling the total delivered energy, over a varying range if load impedances, is needed.

The present invention provides embodiments wherein the voltage on the storage capacitor is monitored during the delivery of a waveform. An energy converter delivers energy from the converter to the patient either by controlling the delivered current or voltage. A preferred waveform is a voltage-controlled waveform that is ascending over time, commonly termed a "ramp" waveform. In another embodiment the ICD, during the delivery of the waveform, measures the total load impedance and then adjusts the shape and duration of the waveform to compensate.

As will become clear, the use of alternative waveforms can improve the defibrillation efficacy of the standard truncated exponential biphasic waveform. These new alternative waveforms include rectangular waveforms as well as ascending ramp waveforms with single or multiple phases. The implementation and feasibility of these waveforms in an ICD, however, demand power conversion circuitry that is both efficient and small.

BRIEF DESCRIPTION OF THE DRAWINGS

FIG. 8 is a set of three equations used to develop the inductor designs mentioned in FIG. 7.

DETAILED DESCRIPTION OF THE DRAWINGS

Figure 1:
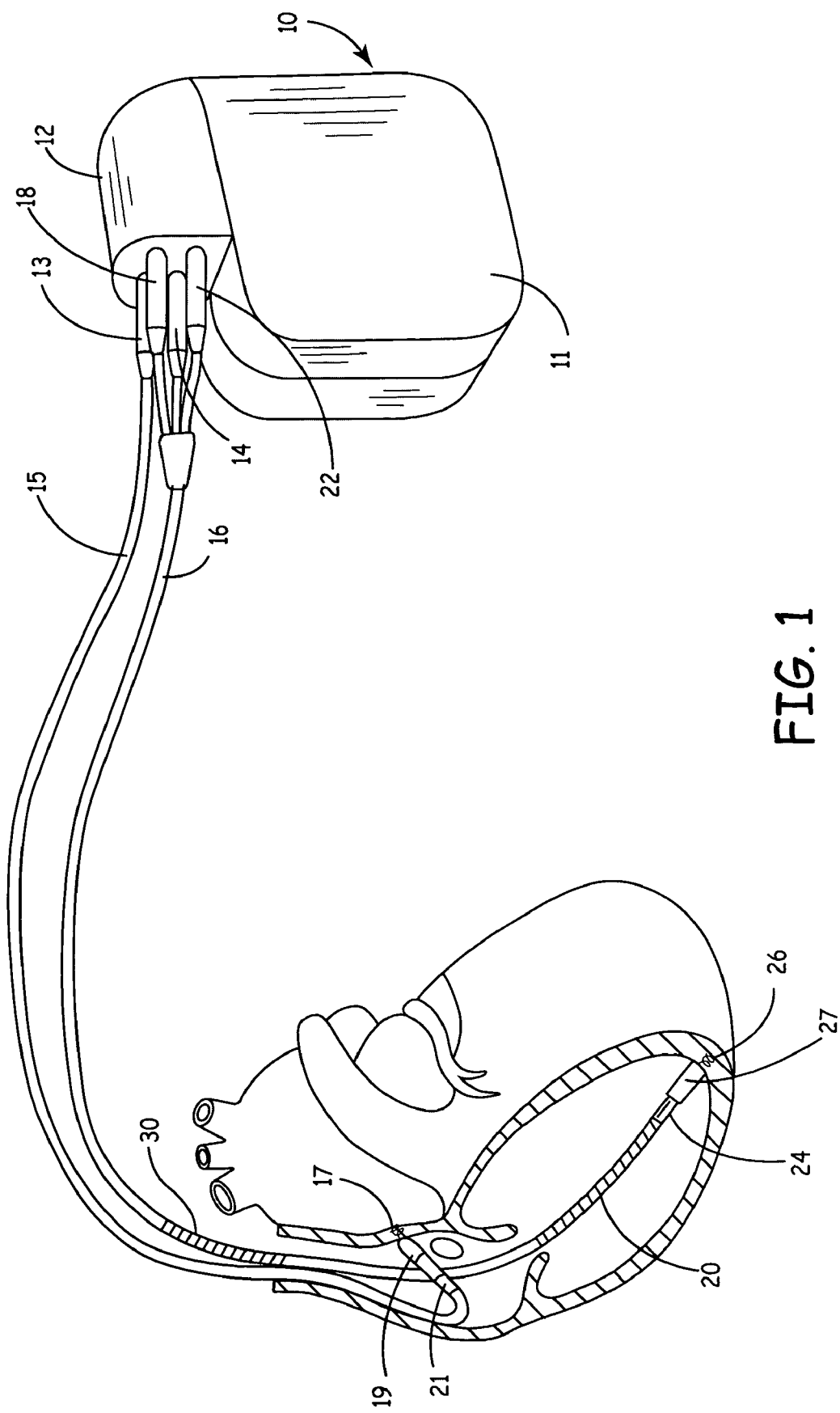
FIG. 1 is an illustration of a ICD type system according to the present invention.

Referring now to FIG. 1, there are illustrated a defibrillator 10 and leads 15 and 16, making up the ICD type system of this invention. The leads shown are illustrative, it being noted that other specific forms of leads are within the scope of this invention. See, for example, U.S. Pat. Nos. 4,932,407 and 5,174,288, as well as U.S. Pat. No. 5,261,400, all of which are incorporated by reference in their entirety. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for sensing ventricular depolarizations. While electrodes 24 and 26 may be used for bipolar pacing and sensing, electrode 26 may be used in conjunction with the surface of device casing 11, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, a superior vena cava (SVC) coil 30, positioned in the subclavian vein, which can be used for electrogram sensing and/or applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 20, 24, 26 and 30.

Atrial lead 15 as illustrated has, located adjacent to the distal end, an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 11, which surface acts as a common or indifferent electrode in what is termed unipolar operation. Note that, in this example, atrial lead 15 is not equipped with coils for use in the sensing and delivery of cardioversion or defibrillation pulses. This is not meant to preclude the inclusion of such applications that may be used advantageously with the present invention.

An implantable ICD type device, or defibrillator 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
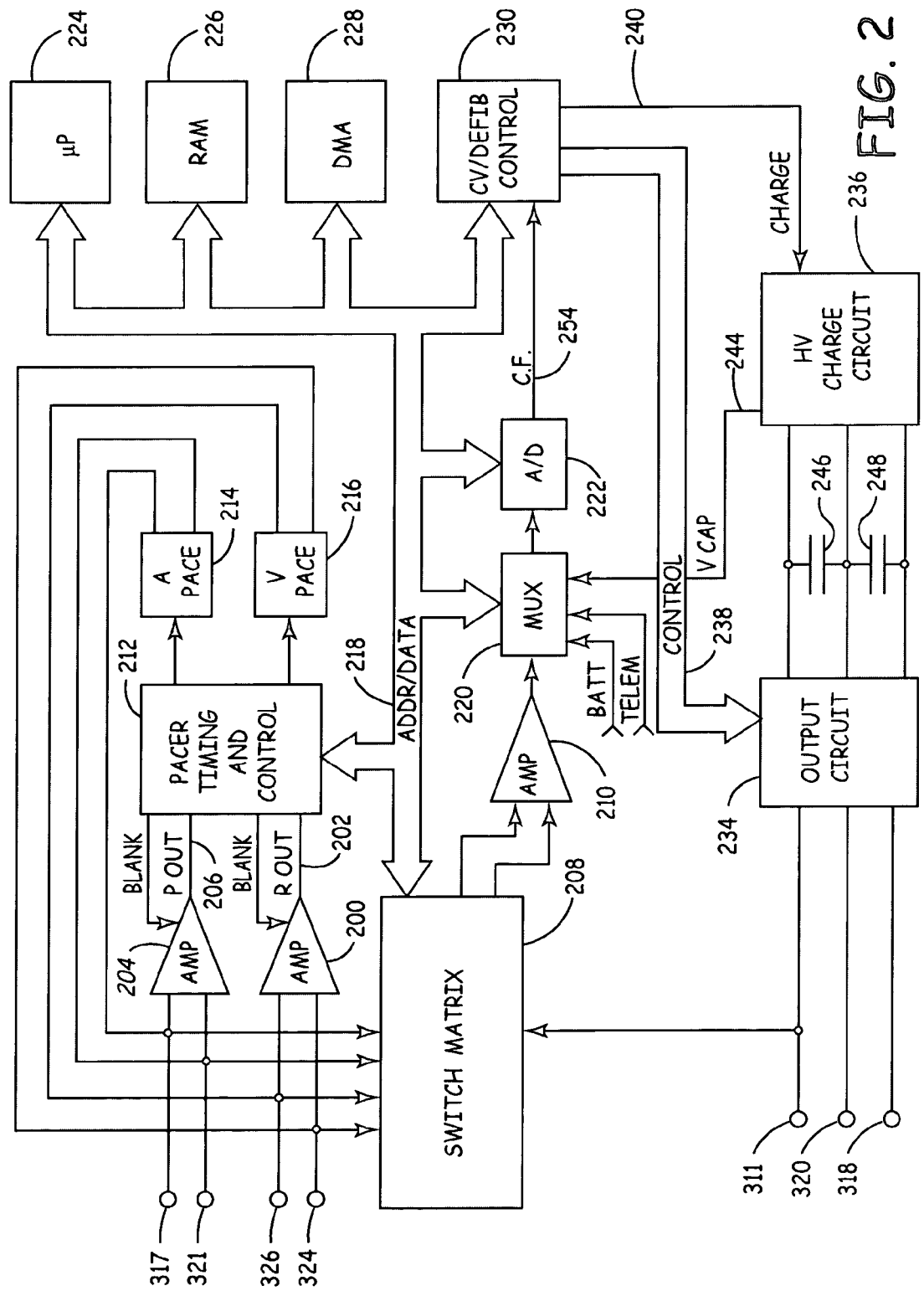
FIG. 2 is a block, functional diagram of an ICD type device adapted to carry out the features of the present invention.

FIG. 2 is a functional schematic diagram of an implantable ICD in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable ICD. Electrode 320 corresponds to electrode 20 and is a defibrillation electrode located in the right ventricle. Electrode 318 corresponds to electrode 30 and is a defibrillation electrode located in the SVC. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The arrhythmia detection method of the ICD may include prior art tachyarrhythmia detection algorithms. As described below, the entire ventricular arrhythmia detection methodology of presently available Medtronic ICDs employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the implantable ICD.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and, in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

Figure 3:
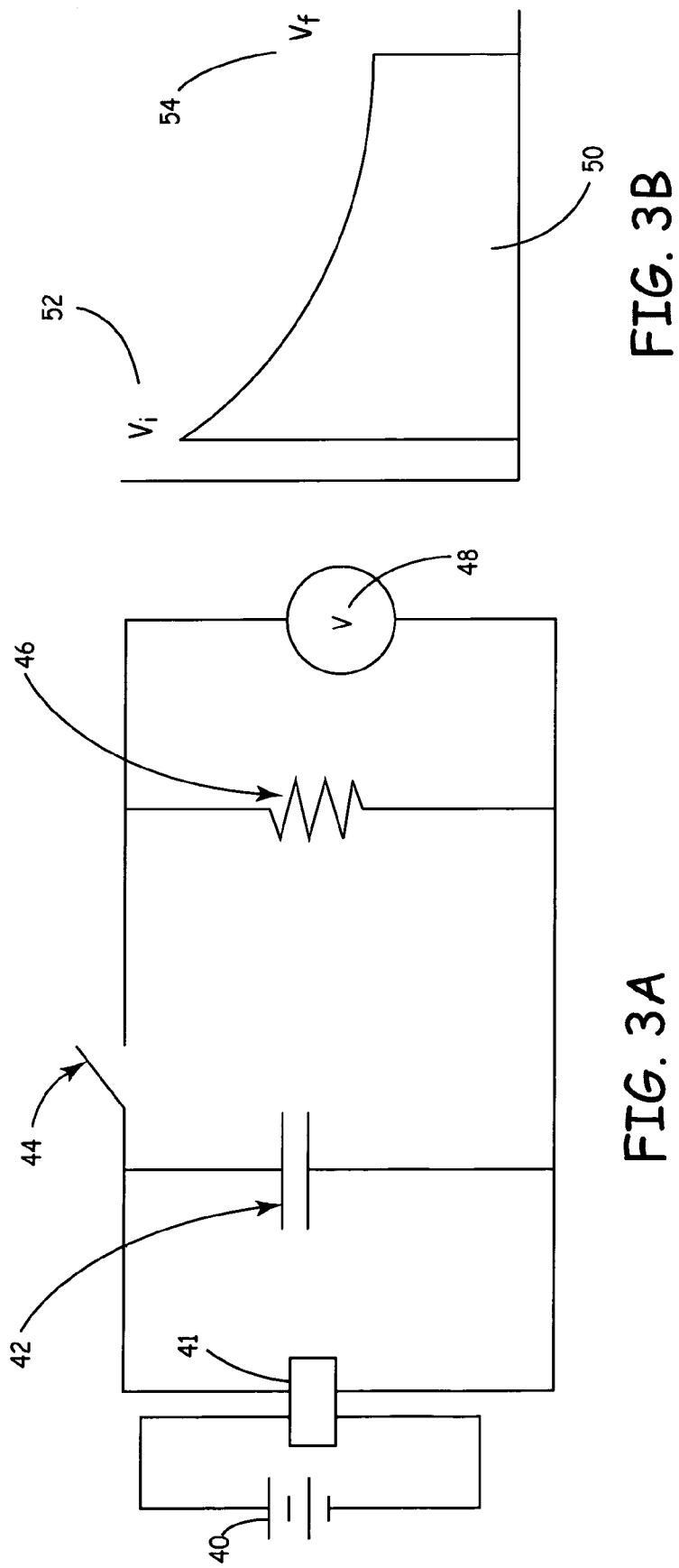
FIG. 3a is a block diagram of the circuit used to generate a truncated exponential waveform used in previous ICDs.
FIG. 3b illustrates a monophasic truncated exponential waveform.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. Refer to FIG. 3a for more detail on output circuit 234 for the delivery of a truncated exponential waveform and to FIG. 5 for the delivery of an arbitrary waveform, which is the subject of the present invention. An example of output circuitry for delivery of biphasic pulse regimens may be found in the above-cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses. On the other hand, circuitry similar to that shown in FIG. 5 of the '883 patent, which is used to generate arbitrary waveforms, e.g., ascending ramp and square waveforms among others will be disclosed as part of the present invention.

In the event that fibrillation is identified, the typical therapy will be the delivery of a high amplitude defibrillation pulse, typically in excess of 5 joules. Lower energy levels may be employed for cardioversion. As in the case of currently available implantable ICDs, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska et al., U.S. Pat. No. 4,727,380, issued to Vollmann et al. and U.S. Pat. No. 4,587,970, issued to Holley et al.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/ control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/ control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al on May 13, 1986, all of which are incorporated herein by reference in their entireties may also be used.

In modern ICDs, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

Referring to FIGS. 3A and 3B, those familiar with the art will recognize that the type of circuit described in FIG. 3a is used to generate monophasic truncated exponential waveform 50 in FIG. 3B. With reference to FIG. 3A, ICD battery 40 provides voltage to capacitor charging circuit 41 which delivers energy to capacitance 42. At the start of the formation of defibrillation waveform, switch 44 closes and a voltage is delivered across patient/resistance 46. In this embodiment, voltage as measured by voltage meter (V) 48 with a trend line defined by $V_i$ 52 and then decays down to $V_f$ 54 as illustrated in FIG. 3B. At some point into the waveform, switch 44 re-opens. Thus, truncating the waveform at $V_f$ 54.

The method in this embodiment is to truncate waveform 50 when voltage ($V_f$) 54 of waveform 50 reaches a certain level. As is understood by those skilled in the art, the voltage of waveform 50 is proportional to the delivered energy. As the voltage decays from initial voltage ($V_i$) 52 to final voltage ($V_f$) 54, equation 1 defines the delivered energy in relation to the voltage left on the capacitor at the beginning of waveform 50.

$$U_i = \tfrac{1}{2} C V_i^2 \quad \text{(Equation 1)}$$

where U=energy, C=capacitance, and V=voltage.

Specifically, Equation 2 defines the energy in relation to $V_f$ 54:

$$U_f = \tfrac{1}{2} C V_f^2 \quad \text{(Equation 2)}$$

where U=energy, C=capacitance, and V=voltage.

As mentioned, the voltage increases at $V_i$ and decreases down to $V_f$. Specifically, when switch 44 opens the waveform is truncated. One aspect of the present invention is determining the point at which the waveform should be truncated. The waveform is truncated by determining the remaining energy on capacitor 42. Algorithmically, the difference between U1 and U2 yields its magnitude of deliverable energy at any given initial and final voltages.

Accordingly, the ICD would deliver the required energy to the load so long as the energy is truncated at the proper final voltage in the waveform. When the voltage on voltage meter 48 reaches the desired final voltage, the switch opens to truncate the waveform.

In another embodiment, called the "fixed tilt method," the amount of leading edge voltage to put on the capacitor before the start of discharge is set during the design and manufacturing stage. Tilt is defined as the percentage by which the voltage decays over the course of the waveform. In a fixed tilt method, the tilt percentage is kept fixed regardless of the load. This would mean in a higher impedance patient, it might take longer to discharge the capacitor, but the waveform is still truncated at the same point. Thus, in fixed tilt method, the delivered energy remains constant.

In either embodiment, the physician merely needs to program the desired energy (in joules) to deliver a waveform commensurate with the programmed value.

When the output voltage or current of the ICD is actively controlled during delivery of a waveform, a new problem arises. The total delivered energy becomes dependent on the load resistance of the patient. Since the ICD pre-stores usable energy on a capacitor, two scenarios, inter alia, could arise that depend on load resistance. First, there may not be enough stored energy to deliver a desired waveform. Alternatively, there may be an excess of usable energy on the storage capacitor after the waveform has been delivered. The first case results in a waveform that is likely distorted or cut off, while, in the latter case, energy with the potential to further improve the defibrillation success rate is wasted.

One of the key aspects of the present invention is to keep a consistent amount of energy delivered to the patient regardless of the changing load in an individual patient or the changing load that one finds clinically from patient to patient. This consistency allows an ICD with active control of the output waveform to use as much stored energy as possible when delivering a waveform. When a physician programs the amount of energy (in joules) that need to be delivered during cardioversion or defibrillation therapy, he should be assured that this amount of energy is being delivered, no matter what the load impedance is within the patient. The present invention ensures that the energy programmed is delivered, regardless of the changing patient load.

Figure 4:
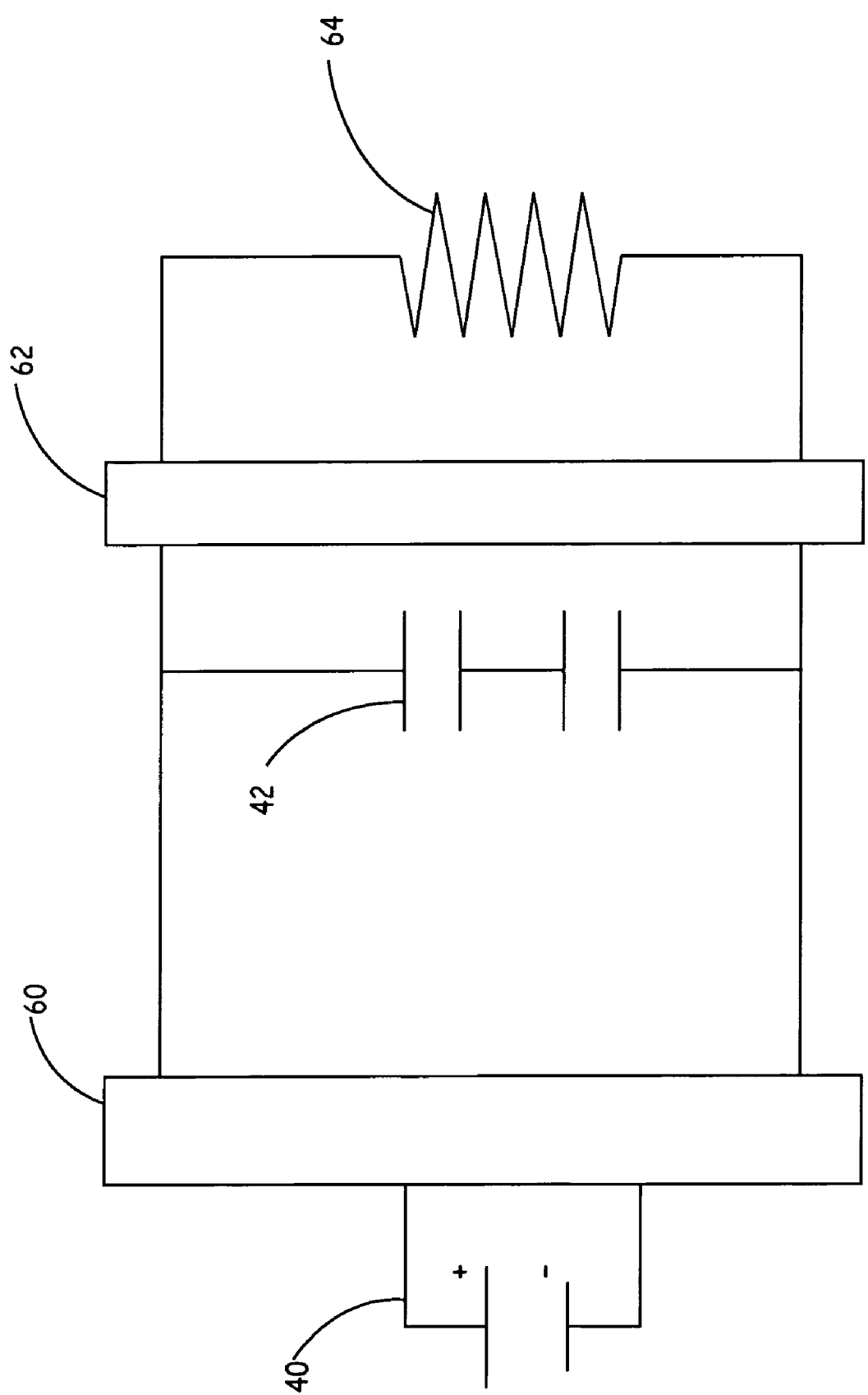
FIG. 4 is a block diagram of the circuit used to generate arbitrary waveforms of the present invention.

FIG. 4 is a block diagram of the circuit implemented to generate arbitrary waveforms of the present invention. ICD battery 40 delivers energy to charging transformer 60 that in turn conveys energy to capacitance 42. At the start of the formation of defibrillation waveform, switching power converter 62 transforms the energy stored in capacitor 42 into any waveform shape (see FIGS. 5 and 6), regardless of patient resistance/load 64.

The switching power converter 62 (see FIG. 7 for details) allows the device to step down the voltage of the output, as well as transforming the energy stored in capacitor 42 into any waveform shape. The amount of energy available at the start is the only constraint. The ICD cannot generate more energy, but in accordance with the present invention, the way the energy is delivered, or the waveform shape can be tailored to meet various requirements. Thus, the issue of changing impedance/load is successfully addressed by the present invention in that the circuit can deliver any waveform shape to the load, and thus deliver consistent energy, irrespective of load impedance.

Current ICDs defibrillate with more energy than generally needed. A useful goal is to use less delivered energy and/or use the available energy more efficiently. If this is attainable, then the ICDs so equipped will achieve the same results with a lower joule output. Current systems achieve their results with truncated exponential waveforms, either monophasic or biphasic. Other waveforms have been shown on a theoretical basis to reduce the amount of energy needed to defibrillate patients. The Huang study, previously mentioned, cites the ramp waveform as one distinct possibility that helps reduce the amount of energy required.

Figure 5:
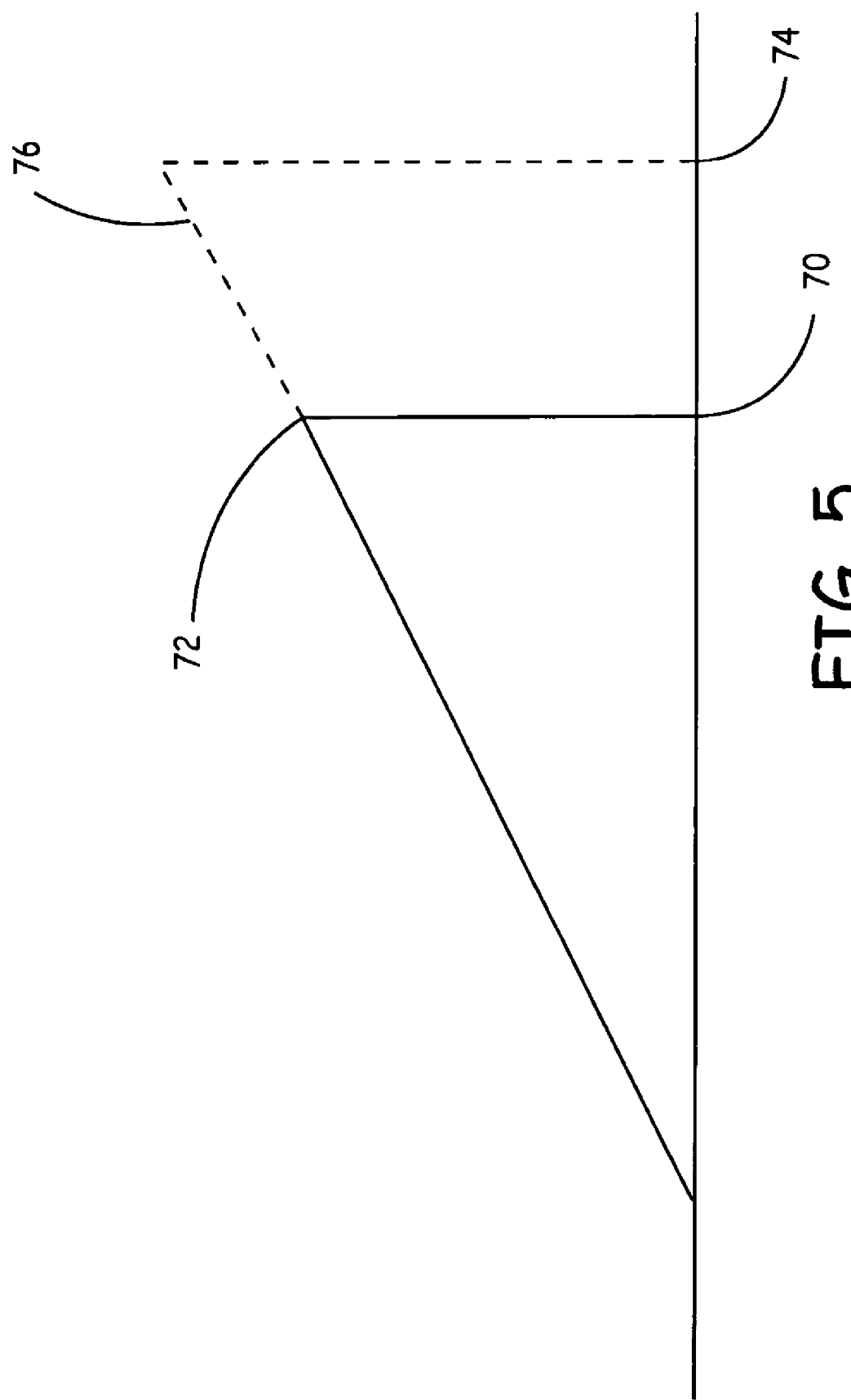
FIG. 5 is an illustration of a ramp waveform used as the first embodiment of the present invention.

FIG. 5 is an illustration of a ramp waveform in accordance with the present invention. In this embodiment, the voltage on the storage capacitor is monitored as a waveform is delivered. The capacitor is precharged to a predetermined voltage and thereby stores a desired amount of energy for delivery of the waveform. Switching power converter 62 (FIG. 4) delivers energy from capacitor to the patient either by controlling the delivered current or the delivered voltage. A preferred waveform is a voltage-controlled waveform that increases gradually over time, similar to the ramp waveform depicted in FIG. 5. This waveform could be controlled with a constant slew rate, in order to allow both pulse width and peak amplitude to compensate for load variation. When the energy converter has consumed a specific amount of energy during the delivery of the waveform determined by the voltage on the capacitor decaying to a certain value the waveform, or a section thereof is truncated in the case of multi-phasic or multi-segmented waveforms. With this preferred waveform, a patient with a larger load impedance will receive a longer waveform 70 to 74, with higher peak voltage 72 to 76. Instead of a voltage-controlled waveform as shown in FIG. 5, a current-controlled output waveform could be used (not shown). Whether it is voltage or current controlled, the result will still be a consistent amount of total energy delivered to the load irrespective of the patient load impedance. As discussed in more detail below with reference to FIG. 4, setting the gradient or rise rate of the ascending waveform and adjusting the charge voltage of the storage capacitor and the storage capacitor voltage at which the waveform is truncated brings about scaling of either a voltage or current-controlled waveform to allow the operator to select the desired energy to be delivered. Accordingly, in the preferred embodiment, the energy converter measures the capacitor voltage without converting it into impedance. Then it truncates the pulse based on delivered energy.

Figure 6:
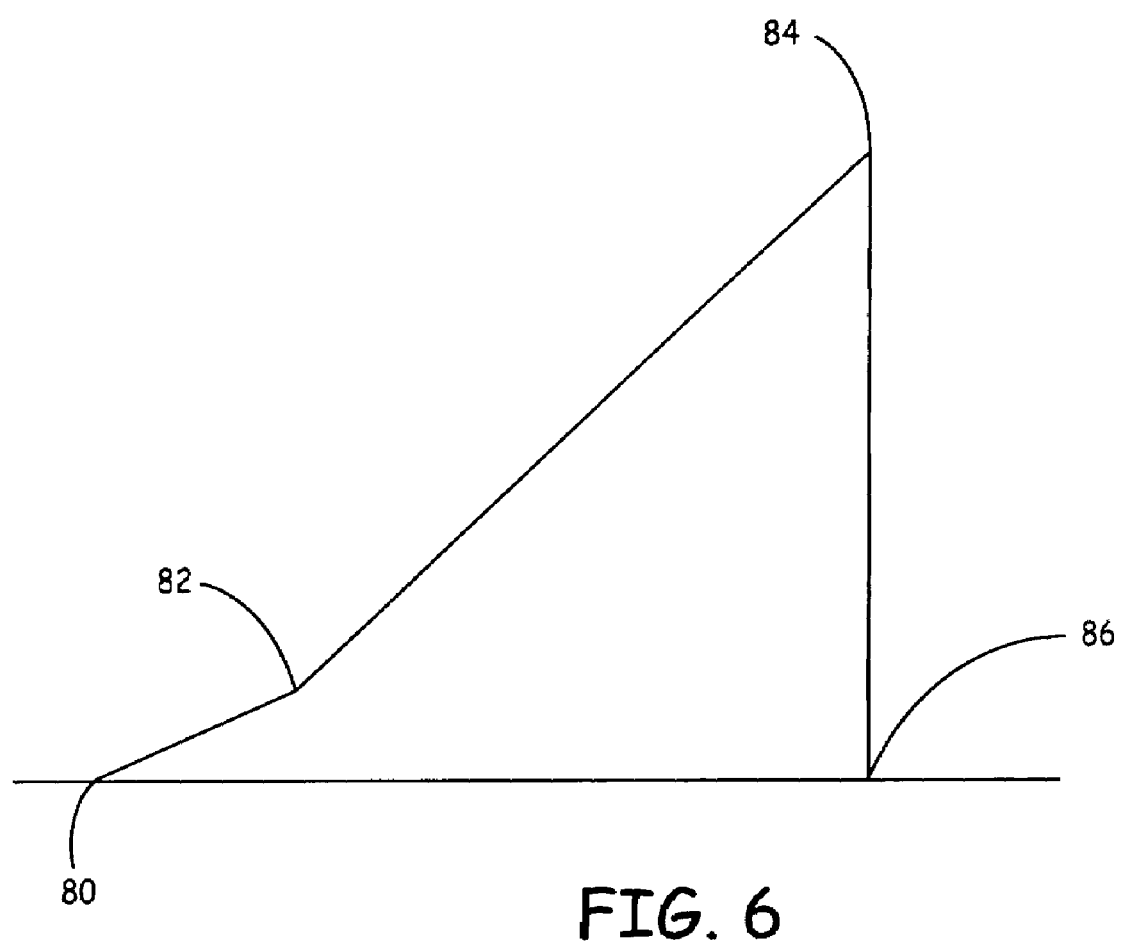
FIG. 6 is an illustration of a ramp waveform used in the second embodiment of the present invention.

FIG. 6 is an illustration of a ramp waveform implemented in yet another embodiment of the present invention. In this embodiment, the device measures the resistance over the time it takes to deliver a small portion of energy 80 to 82.

This results in finding the length of time it takes for the capacitor voltage to decay by a certain percentage. For example, the device could wait to see how long it takes to consume one joule of energy from the capacitor. Then, knowing the voltage of the output waveform for this amount of time, the device can compute in real time the resistance based on equations 3 and 4. Based on this analysis, the energy converter knows how long to extend the pulse 82 to 84 (at time 86) to deliver the programmed level of energy (joules) irrespective of load impedance. One aspect of the present invention is the method of monitoring the delivered energy as a function of time during the first part of the waveform and then using that information to compute the resistance. Once the impedance of the patient is known, the amplitude of the remainder of the waveform is scaled so that the amount of energy delivered by the waveform is consistent. Thus, in FIG. 6, the device delivers a voltage that rises at a certain rate during the first portion of the ramp wave 80 to 82; it is during this portion of the ramp that the device computes the resistance. Then, if the impedance is high, the voltage will rise at a faster rate 82 to 84 than if the resistance is low. In either case, the invention enables the delivery of a consistent amount of energy to a varying load and/or unknown load. One of the beneficial implementations of the present invention relates to changes in implanted devices and patient resistance that occurs over time. For example, a lead may exhibit changes in load or voltage based on age and other factors and the patient's impedance may vary over time. In the face of these variations, the present invention enables the delivered energy output to remain consistent with the desirable energy output.

Turning now to the equations used in this embodiment, the energy converter measures resistance during the waveform by first measuring the length of time d during the waveform that the storage capacitor decays by a certain voltage. This percentage of voltage is used to calculate the delivered energy, $U_t$ to determine a comparator circuit sends a trigger signal when the storage capacitor decays to a certain threshold with a counter circuit keeping track of the elapsed time which is d. If the switching energy converter controls output voltage, the resistance is computed according to the following equation:

$$R = \frac{\int_o^d V^2(t)dt}{\gamma U_t} \quad \text{(Equation 3)}$$

where $\gamma$ is the efficiency of the energy converter, d is the duration required for an energy of $U_t$ to be drawn from the storage capacitor and V(t) is the voltage of the waveform, known before delivery of the shock with a controlled voltage output.

If the switching energy converter controls output current and uses the same method, the resistance is computed according to the following equation:

$$R = \frac{\gamma U_t}{\int_o^d I^2(t)dt} \quad \text{(Equation 4)}$$

where I(t) is the current of the delivered waveform. Once the resistance of the patient is known, the amplitude of the remainder of the delivered waveform is calculated so that the amount of energy delivered by the waveform is consistent with the energy of the storage capacitor. In this embodiment and, whether voltage or current are delivered, the switching energy converter measures the impedance during the initial position of the waveform and then scales the amplitude of the remainder of the waveform.

Figure 7:
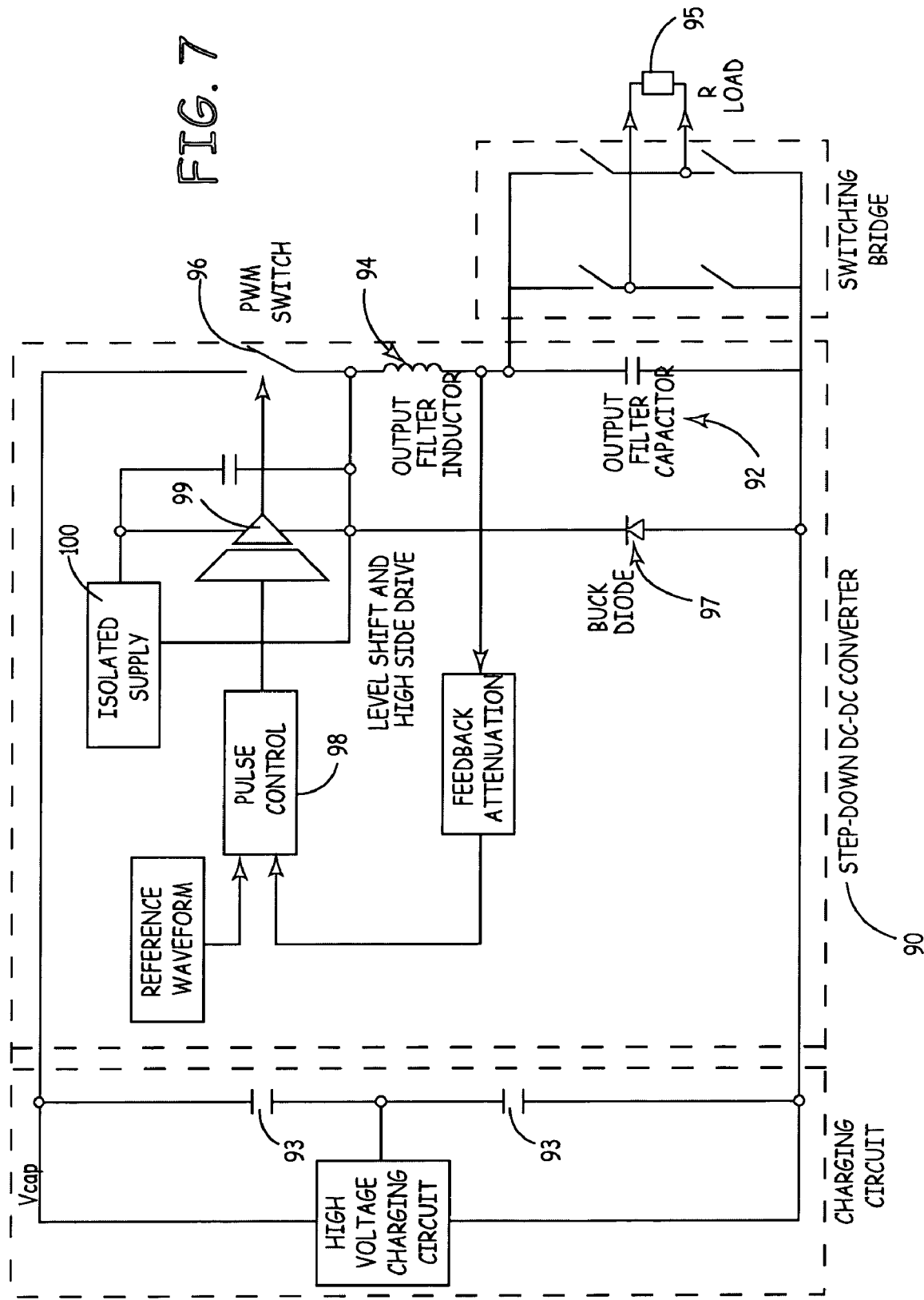
FIG. 7 is a block diagram of the switching power converter used to implement the two embodiments of the present invention.

Turning now to FIG. 7, we turn our attention to the implementation of the arbitrary waveforms via a switching energy converter. High frequency switching converters employed in switch-mode power conversion are useful in this application. In a switching converter, the power transistor is used in a switching mode rather than in the continuous mode employed in a linear supply. Switch mode power converters can be configured in their simplest form as a step-down (buck), step up (boost), or combination buck-boost.

A buck or step-down converter is a power conversion circuit commonly used in dc to dc conversion applications in many industries. Descriptions of such circuits many be found in many texts, including, for example, in *Power Electronics: Converters, Applications and Design*, Mohan, Undeland and Robbins, John Wiley & Sons, New York. In this application, the electrical requirements include high efficiency and small component size to minimize the impact of the circuit on overall system size.

The buck configuration is suited for implementation with the present invention as compared to the boost and buck-boost converters. It has the least demands on the inductor relative to the other two designs.

The converter is shown in one embodiment in FIG. 7. In this implementation, a dc source voltage is maintained on a plurality of hold capacitors 93. The step-down converter uses the dc voltage as a power source. Within the step-down converter a pulse width modulating switch 96 drives an inductor/capacitor filter into a resistive load 95, as is typical in a buck converter, when the switch 96 is closed, current is sourced from the hold capacitor 93 with current increase controlled by the inductor 94 value. When switch 96 is open, the current continues to flow in the inductor 94 and load, forward biasing the diode 97. The control circuit compares the output voltage to a reference waveform and modifies the duty cycle as required to maintain a specific output voltage. The pulse control circuit 98 drives the modulating switch 96 through a level shift and high side drive circuit. In the implementation shown, this is realized with an opto-driver 99. In other embodiments, this might be accomplished with an isolation transformer or a high voltage semiconductor device as isolation, along with drive circuit components. The reference waveform could be provided by an analog reference or in a digitized form and converted by a D/A converter. The control circuit as shown is implemented in an analog format with an error amplifier and pulse width modulation comparator. In another embodiment, it might be implemented with a digital controller. In the implementation shown, the error amplifier has a high dc gain for linearity as well as a low pass pole for control loop stability. Control circuitry (not shown) is required to monitor the voltage on the hold capacitor 93 to determine the point at which the correct energy has been delivered for a given phase and the therapy pulse phase change should occur. This hold capacitor 93 monitor could also determine the point at which the final phase should be terminated. Implementation of the switch could be done with a high voltage BIMOSFET, FET, IGBT, or other switch technology. In a preferred embodiment, the switch is implemented with a high current BIMOSFET switching at 500 kHz. The output filter capacitor 92 is a typical surface mount 0.1 at high voltage capacitor. The diode 97 requires high reverse voltage blocking capability due to applied voltages in the range of 1000 V. It also requires fast recovery characteristics to reduce switching losses. The diode 97 function could also be implemented with a semiconductor switch along with control circuitry to enable it when the switch 96 is off. Design as a synchronous or resonant converter would include such a switch in lieu of diode 97. The isolated supply 100 could be implemented with an isolation transformer, pulse transformer, or bootstrap supply pump.

The switch frequency, peak inductor current, and output ripple voltage define the requirements for the inductor. In a preferred embodiment, inductor 94 is a 0.5 cc stack of two high flux powder cores (torroids) with common winding to provide an inductance of approximately 14 :MH with a common 9 :MH at the 40 Amp peak inductor current. Other materials might be used in inductor 94 as well. The therapy pulse period and duty cycle are low enough that heating effects do not enter into the inductor design requirements. In order to minimize volume and limit the inductance change at 40 Amps, a core permeability as low as possible (14, for example) is necessary.

Implementation of such a converter requires output filtering, and inductor 94 is implanted to provide such a filter. To minimize the impact on the size of the ICD, the size of the inductor must be kept small. Minimizing the inductance value contributes to the overall size reduction. Parameter constraints in the converter design limit the minimum value of the inductance. Beyond this, physical design techniques must be used to reduce the physical size, while still meeting electrical design constraints.

A high voltage buck (step-down) converter 90 may be used in an arbitrary defibrillation waveform generator in an implanted ICD device. Implementation of such a converter requires output filter capacitor 92 which includes inductor 94. To minimize the impact on the size of the implanted device, the physical size of the inductor 94 must be space-volume efficient. Parameter constraints in the converter design will limit the minimum value of inductor 94. Further, physical design techniques must be used to minimize the physical size, while still meeting the electrical design constraints. Inductor electrical constraints for an implanted ICD waveform include tolerance of a significant DC current, 30 amps, for a short duration, <20 ms, with ripple currents of ±10 Amps. Total peak current could therefore be 40 Amps. Heating effects are not significant since the pulse duty cycle is very low. Tolerance of such a current with minimal loss of inductance requires the use of a material such as low permeability high flux powder cores. This material allows significant levels in DC bias while preventing core saturation. Building a magnetic bias into the core could also be used to prevent core saturation.

FIG. 8 is a set of three equations used to develop the inductor designs mentioned in FIG. 8. The inductance for this converter implementation must be in the range of 10–20 :H. A reasonable inductor size to minimize impact to overall device volume is 0.5 cc. The trade-off of low permeability material involves a lower value of inductance per turn of winding. To further optimize the packaging efficiency of the core, a stack of torroid cores with a common winding could be implemented. For a given core, a stack of cores can provide the same inductance with fewer turns that reduces the DC bias effect. The core size can be smaller in diameter with a longer length of stacked cores. This results in a minor improvement in inductor volume for a given inductance value at the specified peak current, as well as a more packaging-efficient aspect ratio. Finally the inductor must not saturate in the presence of externally applied DC magnetic fields less than 1600 Gauss. The distributed air gap of the powder core is ideal for this requirement.

Inductor electrical constraints for a defibrillation waveform include tolerance of a significant DC current (30 Amps) for a short duration pulse (<20 ms) with ripple currents of ±10 Amps. Total peak current could, therefore, be 40 Amps. Heating effects are not significant since the pulse duty cycle is very low. Tolerance of such a current with minimal loss of inductance requires the use of a material such as low permeability, high-flux powder cores. This material allows significant levels in DC bias while preventing core saturation. The inductance for this converter implementation must be in the range if 10–20 H. A reasonable inductor size to minimize impact to overall device volume is 0.5 cc. The trade-off of low permeability material is a lower value of inductance per turn of winding.

To further optimize the packaging efficiency of the core, a stack of toroid cores with a common winding can be implemented. For a given core, a stack of cores can provide the same inductance with fewer turns, which reduces DC bias effects. The core size can be smaller in diameter with a longer length of stacked cores. This results in an improvement in inductor volume for a given inductance value at the specified peak current, as well as a more packaging-efficient aspect ratio. Finally, the inductor must not saturate in the presence of externally applied DC magnetic fields less than 1600 Gauss. The distributed air gap of the power core is ideal for this requirement.

For example, the material required to design a 14 H inductor for 40 Amps of peak current with a volume near 0.5 cc may be sized according to the following formula:

$$N = 1000 \times [L/(s \times A_L)]^{0.5}$$

$$H = (0.4 * PI * N * Ip)/Ie$$

Where: N=number of turns
L=inductance
s=number of stacked teroids
$A_L$=core inductance (:H) per turn squared
H=magnetizing force (in Oersteds)
Ip=peak current
Ie=core magnetic path length
Volume=$PI(dia/2)^2 * ht$ Minimum wire gauge assumed to be 29 AWG. Adiabatic wire heating calculations show this to be reasonable for copper.

Figure 9:
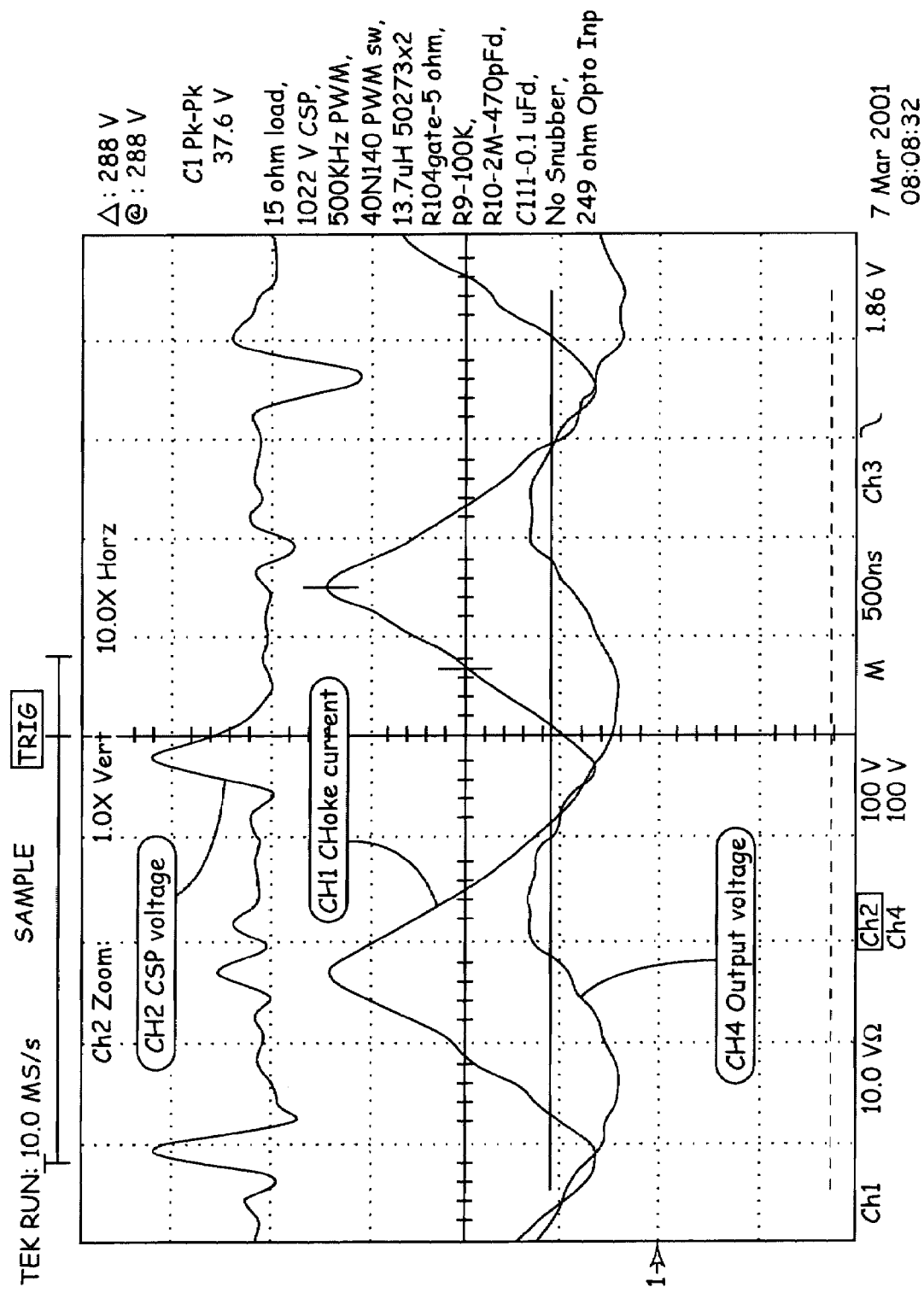
FIG. 9 displays the inductor current in the application at a switching frequency of 500 kHz.

The measurement of inductor 94 (in FIG. 8) using example 3 as implemented with 23 turns is:
L@100 kHz RDC@100 kHz
13.8:H 250 Ohms FIG. 9 illustrates the inductor current in the application at a switching frequency of 500 kHz. In FIG. 9, peak inductor current is 35 Amps (labeled CH1 Choke Current) with no significant change in current slope. This, and other testing, indicates a stable inductance value over the current range. Inductance is calculated as (Vcsp−Vout)*(time change/current change. So, the value of inductance in this case is:

$$L = (580 - 240) * (400 \, nS/14A) = 9.7 \, :H$$

This indicates that the inductor is performing consistent with the calculations shown herein above. No peaking of the waveform was observed, indicating there was no tendency to saturate at this current level. Further testing in the presence of a DC magnetic field resulted in no significant change.

Figure 10:
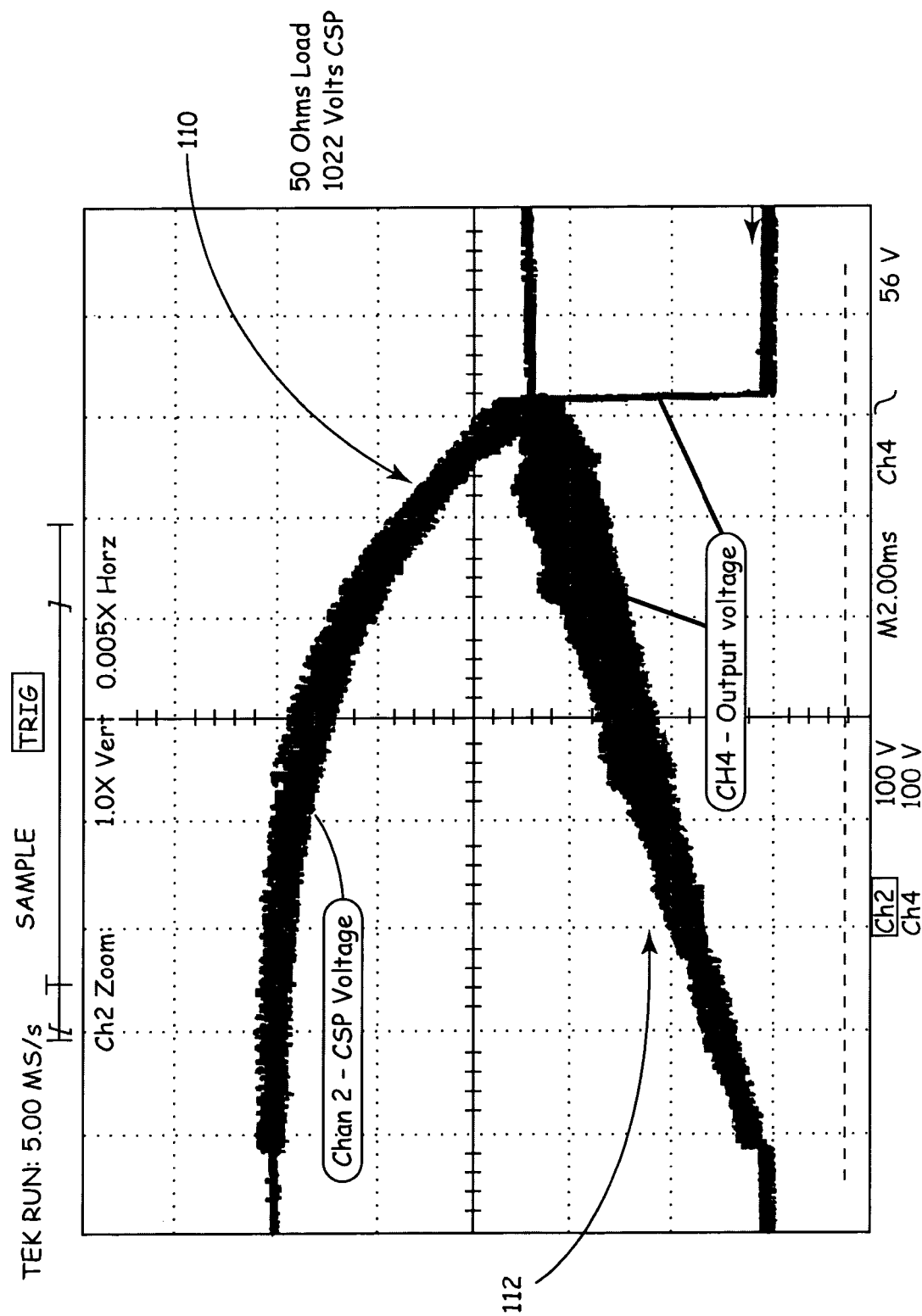
FIG. 10 is an illustration of the delivery of a voltage discharge into a 50-ohm load with a resultant ascending, ramp waveform.

FIG. 10 is an illustration of the delivery of a voltage discharge into a 50-ohm load with a resultant ascending, ramp waveform. This figure shows that CSP voltage 110 applied to a load, consistent with the present invention, results in an ascending, ramp waveform labeled output voltage 112, as depicted in this oscilloscope tracing.

In summary, one "duty cycle" embodiment of the present invention involves delivering an arbitrary waveform to a subject while monitoring the voltage on the energy storage capacitor in the defibrillator. By knowing the voltage on this capacitor before delivery and the size of the capacitor, one knows the total stored energy of the device. One then can deliver a specific amount of energy irrespective of the load resistance by truncating the arbitrary waveform after the voltage on this storage capacitor decays to a threshold value. The energy equations are listed as equation 1 and 2 in the text (above). When using an ideal (i.e., 100% efficiency) step-down, or buck, switching converter, the duty cycle of the power converter is equal to the output voltage over the input voltage. Thus, as an alternative to monitoring the input voltage to determine truncation point, one simply monitors the output voltage and duty cycle and calculates when the input voltage drops to a predetermined value.

In another embodiment of the present invention, a small portion of energy of the waveform is delivered by again monitoring the voltage on the storage capacitor (or using the above mentioned "duty cycle" method). The length of time required to deliver this portion of energy is measured and then used to calculate the load resistance according to equation 3 or 4 (above) depending on whether we are controlling electrical current or voltage. Knowing the resistance (or impedance) of the patient and knowing the shape and duration of the waveform desired to be delivered, one can then rescale the remainder of that waveform to ensure delivery of a predefined, desired amount of energy.

The present invention may be implemented in an implantable medical device, an external medical device and may be used in conjunction with chronic or acute arrhythmia detection schemes and/or cardiac therapy delivery.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

We claim:

1. A system for controlling a slow-rise, ramp-type defibrillation output waveform to deliver constant energy from a device to terminate a cardiac fibrillation condition, comprising:
    means for delivering an initial portion of energy to a load impedance of a subsystem between at least a pair of electrodes with a voltage-controlled or current-controlled slow-rise, ramp-type defibrillation output waveform;
    means for measuring a length of time it takes a storage capacitor voltage to decay by a certain percentage during delivery of the initial portion of energy;
    means for calculating a real-time value of the load impedance that a voltage-controlled or current-controlled slow-rise, ramp-type defibrillation output waveform is delivered into based on the length of time; and
    means for extending the voltage-controlled or current-controlled slow-rise, ramp-type defibrillation output waveform to deliver a pre-programmed level of energy irrespective of the load impedance.

2. A system according to claim 1, wherein said means for extending includes a power converter circuit.

3. A system according to claim 1, wherein one electrode of the pair of electrodes is a portion of an electrically conducting canister for an implantable medical device.

4. A system according to claim 1, wherein said pre-programmed level of energy is a set of discrete pre-programmed energy levels and each successive member of said set has a greater magnitude than the previous member of said set.

5. A system according to claim 1, wherein said voltage-controlled or current-controlled slow-rise, ramp-type defibrillation output waveform comprises at least one of the following waveforms: an ascending amplitude waveform, a pair of bi-phasic slow-rise, ramp-type defibrillation output waveforms, a first reverse polarity descending amplitude, slow-rise, ramp-type defibrillation output waveform, a truncated slow-rise, ramp-type defibrillation output waveform, a multi-phase slow-rise, ramp-type defibrillation output waveform, a multi-phasic slow-rise, ramp-type defibrillation output waveform.

6. A system according to claim 1, wherein said means for extending the voltage-controlled or current-controlled slow-rise, ramp-type defibrillation output waveform includes a switching converter.

7. A system according to claim 6, wherein the switching converter includes at least one of the following: a step-down or buck converter, a step-up or boost converter, a combined step-down/step-up or buck-boost converter.

8. A system according to claim 1, wherein the pair of electrodes includes at least one of the following: a percutaneous electrode, a subcutaneous electrode, an epicardial electrode, an endocardial electrode, a transcutaneous electrode, a surface electrode, a canister electrode, a coil electrode, a ring electrode, a tip electrode.

9. A system of delivering constant energy to stabilize a cardiac rhythm in a patient, comprising:
    means for monitoring a portion of a delivered energy being delivered to a portion of cardiac tissue of a patient using an arbitrary, slow-rise, ramp-type defibrillation output waveform in an attempt to successfully terminate an arrhythmia;
    means for calculating a load impedance value of said patient based on a length of time required to deliver the portion of the delivered enemy using the arbitrary, slow-rise, ramp-type defibrillation output waveform; and
    means for adjusting a remaining portion of the delivered energy supplied by the arbitrary, slow-rise, ramp-type defibrillation output waveform based on scaling an amplitude characteristic of the remaining portion of the delivered energy according to the calculated load impedance value of said patient so a desired amount of energy is delivered.

10. A system according to claim 9, wherein said means for monitoring includes means for monitoring the remaining portion of the delivered energy as a function of time.

11. A system according to claim 9, wherein said means for adjusting includes means for controlling a voltage parameter or current parameter of the arbitrary, slow-rise, ramp-type defibrillation output waveform to substantially match the load impedance to thereby deliver a consistent amount of energy.

12. A system according to claim 9, further including:
means for monitoring the portion of cardiac tissue to determine if the arrhythmia has successfully terminated, and if not, operating the means for monitoring the portion of the delivered energy, the means for calculating and the means for adjusting to repeat the functions set forth in claim 9.

13. A system according to claim 12, wherein the means for monitoring the portion of the delivered energy, the means for calculating and the means for adjusting are operated to repeat the functions set forth in claim 9 such that a second desired constant amount of energy is delivered that is greater in magnitude than the desired constant amount of energy.

14. A system according to claim 9, wherein the means for calculating a load impedance value includes at least a pair of electrodes disposed about the portion of cardiac tissue.

15. A method of delivering a desired, predetermined and constant amount of energy to a volume of tissue via a slow-rise, ramp-type defibrillation output waveform, comprising:
charging a storage capacitor;
delivering an arbitrary, slow-rise, ramp-type defibrillation output waveform from the storage capacitor to the volume of tissue through a switching power converter circuit;
calculating a load impedance of the volume of tissue based on characteristics associated with the delivery of the arbitrary, slow-rise, ramp-type defibrillation output waveform from the storage capacitor; and
in response to the calculated load impedance, adjusting the arbitrary, slow-rise, ramp-type defibrillation output waveform so that a predetermined amount of energy is ultimately delivered to the portion of tissue.

16. A method according to claim 15, wherein the arbitrary, slow-rise, ramp-type defibrillation output waveform includes at least one of the following: an ascending amplitude slow-rise, ramp-type defibrillation output waveform, a bi-phasic slow-rise, ramp-type defibrillation output waveform, a voltage-controlled slow-rise, ramp-type defibrillation output waveform, a current-controlled slow-rise, ramp-type defibrillation output waveform, a reverse polarity slow-rise, ramp-type defibrillation output waveform, a truncated slow-rise, ramp-type defibrillation output waveform, a multi-phase slow-rise, ramp-type defibrillation output waveform, a multi-phasic, slow-rise, ramp-type defibrillation output waveform.

17. A method according to claim 15, wherein the method is performed by a device selected from the following list: an automatic external defibrillator, an implantable medical device, an implantable-cardioverter defibrillator, a pacemaker.

* * * * *